(12) United States Patent
Abdelgany

(10) Patent No.: US 8,182,509 B2
(45) Date of Patent: May 22, 2012

(54) SPINAL ROD INSERTION METHOD

(75) Inventor: Mahmoud F. Abdelgany, Rockaway, NJ (US)

(73) Assignee: Custom Spine, Inc., Parsippany, NJ (US)

( * ) Notice: Subject to any disclaimer, the term of this patent is extended or adjusted under 35 U.S.C. 154(b) by 49 days.

(21) Appl. No.: 12/954,287

(22) Filed: Nov. 24, 2010

(65) Prior Publication Data

US 2011/0071571 A1    Mar. 24, 2011

Related U.S. Application Data

(62) Division of application No. 11/193,737, filed on Jul. 29, 2005, now Pat. No. 7,871,424.

(60) Provisional application No. 60/683,698, filed on May 23, 2005.

(51) Int. Cl.
*A61B 17/00* (2006.01)

(52) U.S. Cl. ........................................ 606/206; 606/103

(58) Field of Classification Search .......... 606/205–208, 606/261–278, 103, 99, 86 A, 250–260; 81/424.5, 81/426, 426.5; 294/99.2, 902

See application file for complete search history.

(56) References Cited

U.S. PATENT DOCUMENTS

| | | | |
|---|---|---|---|
| 1,506,675 A | 8/1924 | Seppman | |
| 1,612,474 A | 12/1926 | Strain | |
| 2,314,884 A | 3/1943 | Klein | |
| 4,312,337 A | 1/1982 | Donohue | |
| D273,326 S | 4/1984 | Peterson et al. | |
| 4,475,544 A | 10/1984 | Reis | |
| 4,526,172 A | 7/1985 | Stephenson | |
| 5,102,412 A * | 4/1992 | Rogozinski | 606/86 A |
| 5,250,050 A | 10/1993 | Poggie et al. | |
| 5,591,167 A * | 1/1997 | Laurain et al. | 606/86 A |
| 5,728,112 A | 3/1998 | Yoon | |
| 6,010,509 A | 1/2000 | Delgado et al. | |
| 6,036,692 A | 3/2000 | Burel et al. | |
| 6,159,217 A | 12/2000 | Robie et al. | |
| 6,733,508 B1 | 5/2004 | Propp et al. | |
| 7,871,424 B2 * | 1/2011 | Abdelgany | 606/207 |
| 2001/0053911 A1 | 12/2001 | Hehli et al. | |
| 2002/0188297 A1 | 12/2002 | Dakin et al. | |
| 2003/0040746 A1 | 2/2003 | Mitchell et al. | |
| 2003/0225422 A1 * | 12/2003 | Mosnier et al. | 606/151 |
| 2005/0085812 A1 * | 4/2005 | Sherman et al. | 606/61 |
| 2005/0090824 A1 * | 4/2005 | Shluzas et al. | 606/61 |
| 2005/0277934 A1 * | 12/2005 | Vardiman | 606/61 |
| 2006/0004367 A1 | 1/2006 | Alamin et al. | |

\* cited by examiner

*Primary Examiner* — Eduardo C Robert
*Assistant Examiner* — Jan Christopher Merene
(74) *Attorney, Agent, or Firm* — Rahman LLC (57) ABSTRACT

A method includes loading a longitudinal member comprising holes located at distal ends of the longitudinal member into a holder, the holder comprising a tip end comprising a first portion and a second portion, wherein any of the first portion and the second portion comprise a prong tip; a handle end located distally away from the tip end, wherein the handle end comprises a first gripping arm and a second gripping arm; and an engaging member operatively connecting the first gripping arm to the second gripping arm, wherein the engaging member comprises tooth-like features. The method further comprises engaging the tooth-like features of the engaging member with the second gripping arm; and fitting the prong tip of any of the first and second portions of the tip end of the holder into a hole of the longitudinal member.

13 Claims, 9 Drawing Sheets

SPINAL ROD INSERTION METHOD

CROSS REFERENCE TO RELATED APPLICATION

This application is a divisional of U.S. patent application Ser. No. 11/193,737, now U.S. Pat. No. 7,871,424, filed on Jul. 29, 2005, which claims the benefit of U.S. Provisional Patent Application No. 60/683,698 filed on May 23, 2005, the contents of which in their entireties are herein incorporated by reference.

BACKGROUND

1. Technical Field

The embodiments of the invention generally relate to medical devices, and, more particularly, to medical devices used for spinal implant surgeries.

2. Description of the Related Art

Figure 1:
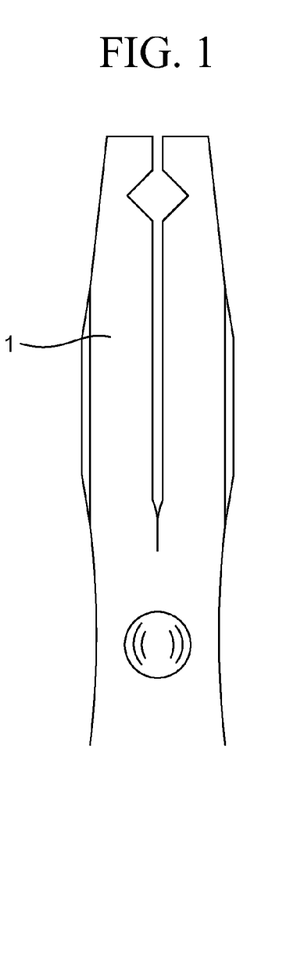
FIG. 1 illustrates a schematic diagram of a conventional rod holder tip.
Figure 2:
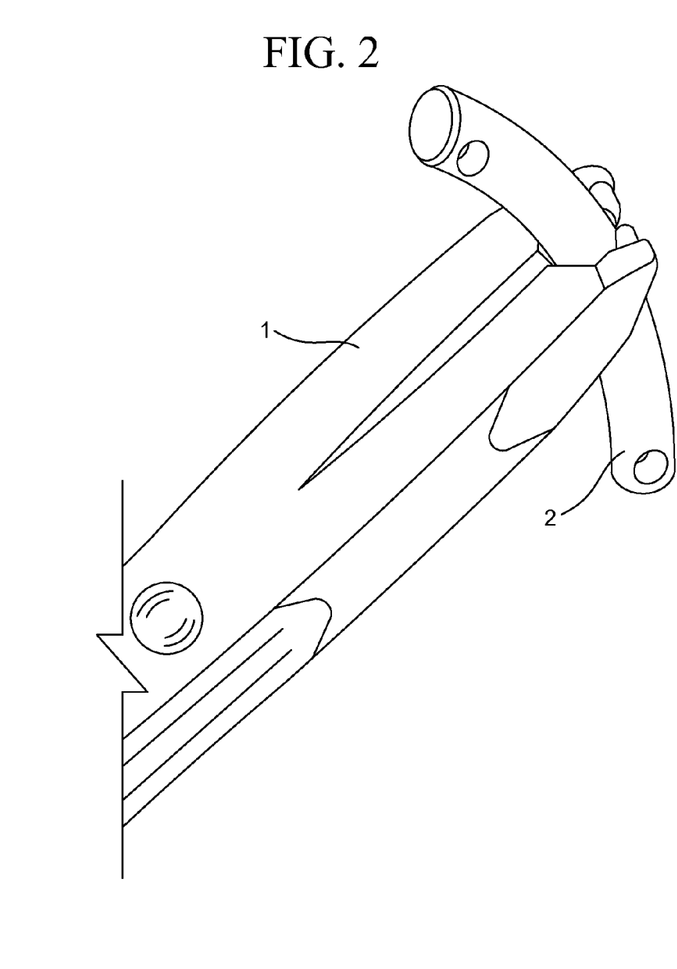
FIG. 2 illustrates a schematic diagram of a conventional rod holder manipulating a rod.

Conventional rod holders and rod inserters can generally only insert a spinal rod into an incision from the middle of the rod where the rod is horizontal to the floor. FIG. 1 illustrates a schematic diagram of a conventional rod holder tip 1. FIG. 2 illustrates a schematic diagram of the conventional rod holder tip 1 of FIG. 1 manipulating a rod 2, wherein the rod 2 is generally held in place by grasping the middle of the rod 2. With the rod 2 in the horizontal position, this would generally require a surgeon to make a large incision in the patient in order to "drop" the rod 2 down into a spinal construct. Accordingly, it is preferable if the size of the incision can be reduced, yet still accommodate a spinal rod. Therefore, there is a need for a novel spinal rod inserter for use in spinal surgeries, which can insert a rod in a smaller-sized incision.

SUMMARY

In view of the foregoing, an embodiment herein provides a method of inserting a longitudinal member in a bone anchor positioned in a vertebral body, the method comprising loading a longitudinal member comprising holes located at distal ends of the longitudinal member into a holder, the holder comprising a tip end comprising a first portion and a second portion, wherein any of the first portion and the second portion comprise a prong tip; a handle end located distally away from the tip end, wherein the handle end comprises a first gripping arm and a second gripping arm; and an engaging member operatively connecting the first gripping arm to the second gripping arm, wherein the engaging member comprises tooth-like features. The method further comprises engaging the tooth-like features of the engaging member with the second gripping arm; and fitting the prong tip of any of the first and second portions of the tip end of the holder into a hole of the longitudinal member.

The method may further comprise positioning the longitudinal member to be parallel to the holder; and inserting the longitudinal member vertically into a desired location in the vertebral body. The second gripping arm may comprise a protruding member, and the method may further comprise engaging the protruding member of the second gripping arm with the tooth-like features of the engaging member. Each of the first portion and the second portion of the tip end may comprise a notch dimensioned and configured to form a generally square hole when the first portion and the second portion are in a closed position. The method may further comprise pivoting the first gripping arm relative to the second gripping arm. The method may further comprise pivoting the first portion relative to the second portion. The method may further comprise rotating the longitudinal member when the longitudinal member is engaged by the prong tip.

Another embodiment provides a method of using a medical device in a surgical procedure, the method comprising providing a longitudinal member comprising a single, generally cylindrical and uniformly constructed rod, with a single first hole bored through a first end of the rod and a single second hole bored through a second end of the rod, wherein the rod is positioned along a longitudinal axis of the longitudinal member, and the hole is positioned transverse to the longitudinal axis of the longitudinal member; providing a holder comprising a first tip end comprising a first portion comprising a first portion sloping wall and a first base continuously coupled to the first portion and stacked atop the first portion, the first base comprising a single outwardly projecting unslotted first prong tip continuously coupled the first base and stacked atop the first base and configured to engage the first hole of the longitudinal member, the first prong comprising a first prong sloping wall comprising a first planer surface at an oblique angle from the first base; a second tip end comprising a second portion comprising second portion sloping wall and a second base continuously coupled to the second portion and stacked atop the second portion, the second base comprising a single outwardly projecting unslotted second prong tip continuously coupled the second base and stacked atop the second base and configured to engage the second hole of the longitudinal member, the second prong comprising a second sloping wall comprising a planer surface at an oblique angle from the second portion; a handle end located distally away from the first tip end and the second tip end, wherein the handle end comprises a first gripping arm and a second gripping arm, wherein the first gripping arm comprises a first curved end forming a 90 degree curve pointing in a direction parallel to and away from the first prong tip and the second gripping arm comprises a second curved end forming a 90 degree curve pointing in a direction parallel to and away from the second prong tip; and an engaging member operatively connecting the first gripping arm to the second gripping arm, wherein the engaging member comprises tooth-like features positioned facing the tip end, wherein the first portion sloping wall and the first prong sloping wall form a first-wedge comprising 45 degree angle, and wherein the second portion sloping wall and the second prong sloping wall form a second wedge comprising a 45 degree angle. The method further comprises engaging the tooth-like features of the engaging member to the curved end of the second gripping arm.

The second gripping arm may comprise a protruding member dimensioned and configured to engage that engages the tooth-like features of the engaging member. The first wedge and the second wedge may comprise a notch that forms a generally diamond-shaped hole when the first portion and the second portion are in the closed position. The first portion and the second portion may rotate about a fixed axis with respect to one another. The method may further comprise operatively connecting the first portion to the second portion. The first prong tip and second prong tip may each be cylindrically-shaped. The longitudinal member may be rotatable when engaged by the first prong tip and the second prong tip.

Another embodiment provides a method comprising providing a medical device comprising a pair of arms comprising a first arm and a second arm, wherein each arm comprises a tip end comprising a tip end sloping wall, the tip end sloping wall comprises a first 45 degree sloping surface, and a tip holder coupled to the tip end and stacked atop the tip end, the tip holder comprising a base coupled to the tip holder and stacked atop the tip holder, the base comprising an outwardly projecting unslotted prong tip stacked atop the base, wherein the prong tip comprises a prong tip sloping wall, the prong tip sloping wall comprises a second 45 degree sloping surface, and the tip end sloping wall and the prong tip sloping wall form a 90 degree wedge therebetween; a handle end located distally away from each the tip end, wherein each the handle end comprises a gripping arm, wherein each gripping arm comprises a curved end forming a 90 degree curve pointing in a direction parallel to and away from the prong tip of each the tip end corresponding to each the handle end, and wherein the handle end terminates where the curved end is in a direction parallel to and away from the prong tip of each the tip end corresponding to each the handle end. The method further comprises operatively connecting the pair of arms together using an engaging member comprising tooth-like features positioned facing the tip end.

The gripping arm may comprise a protruding member that engages the tooth-like features of the engaging member. The tip end of each arm may further comprise a notch and the notch of the tip end forms a square hole when the pair of arms are in a closed position. The method may further comprise operatively connecting the pair of arms together. The method may further comprise providing only one pivoting connection between the tip ends. The tooth-like features of the engaging member may be dimensioned and configured to engage the curved end of one the gripping arm.

These and other aspects of the embodiments of the invention will be better appreciated and understood when considered in conjunction with the following description and the accompanying drawings. It should be understood, however, that the following descriptions, while indicating preferred embodiments of the invention and numerous specific details thereof, are given by way of illustration and not of limitation. Many changes and modifications may be made within the scope of the embodiments of the invention without departing from the spirit thereof, and the embodiments of the invention include all such modifications.

BRIEF DESCRIPTION OF THE DRAWINGS

The embodiments of the invention will be better understood from the following detailed description with reference to the drawings, in which.

DETAILED DESCRIPTION

The embodiments of the invention and the various features and advantageous details thereof are explained more fully with reference to the non-limiting embodiments that are illustrated in the accompanying drawings and detailed in the following description. It should be noted that the features illustrated in the drawings are not necessarily drawn to scale. Descriptions of well-known components and processing techniques are omitted so as to not unnecessarily obscure the embodiments of the invention. The examples used herein are intended merely to facilitate an understanding of ways in which the embodiments of the invention may be practiced and to further enable those of skill in the art to practice the embodiments of the invention. Accordingly, the examples should not be construed as limiting the scope of the embodiments of the invention.

As mentioned, there remains a need for a novel spinal rod inserter for use in spinal surgeries, which can insert a rod in a smaller-sized incision. The embodiments of the invention achieve this by providing a rod inserter that may function as a traditional rod inserter or as a minimal access/invasive rod inserter for spinal surgery, and more specifically a rod inserter that holds a rod in a vertical or semi-vertical position from one end and allows the rod to be inserted and then rotated into its final horizontal position inside a wound. Referring now to the drawings, and more particularly to FIGS. 3(A) through 9, there are shown preferred embodiments of the invention.

Figure 3A:
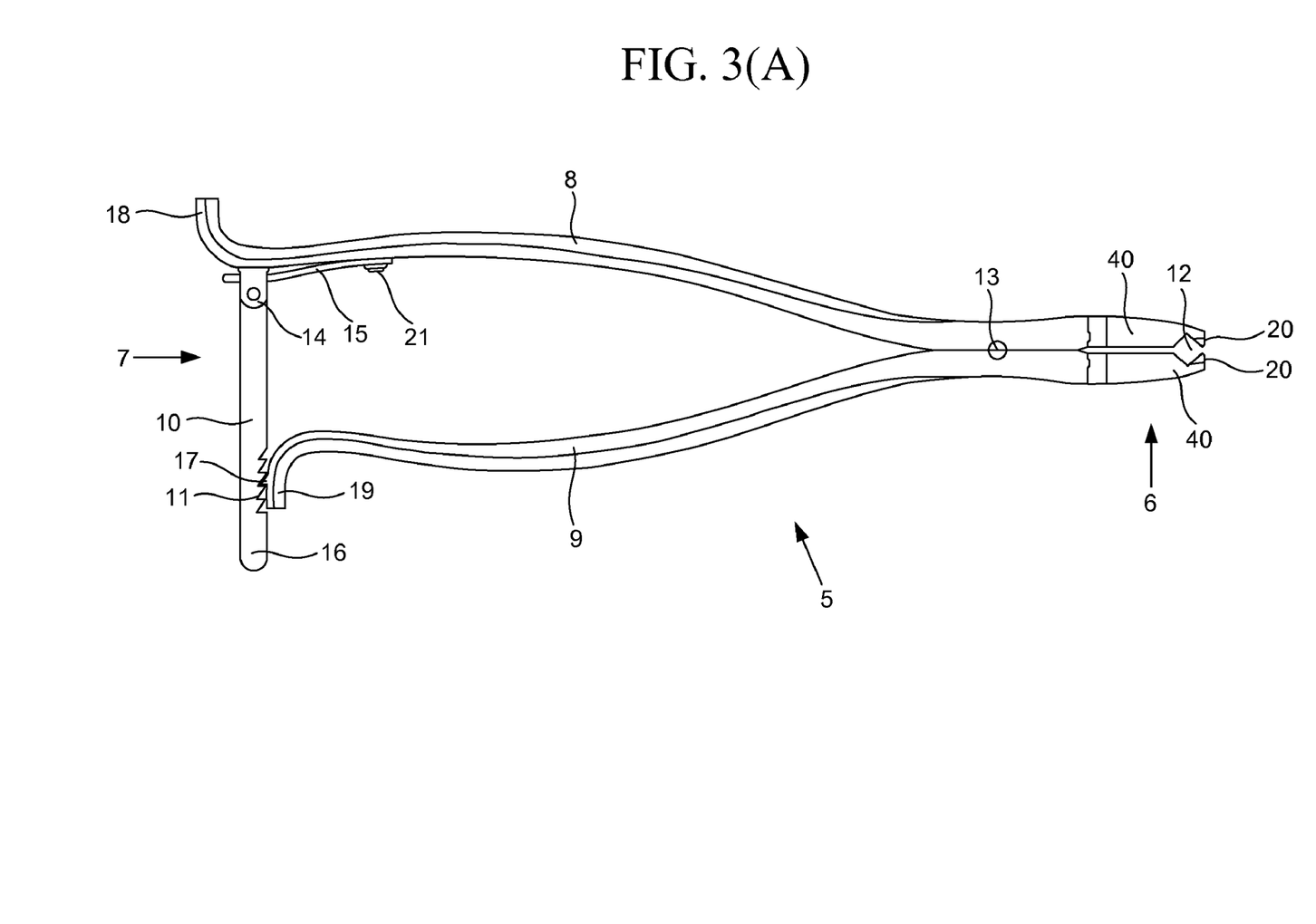
FIGS. 3(A) and 3(B) illustrate schematic diagrams of a rod holder according to an embodiment of the invention.
Figure 3B:
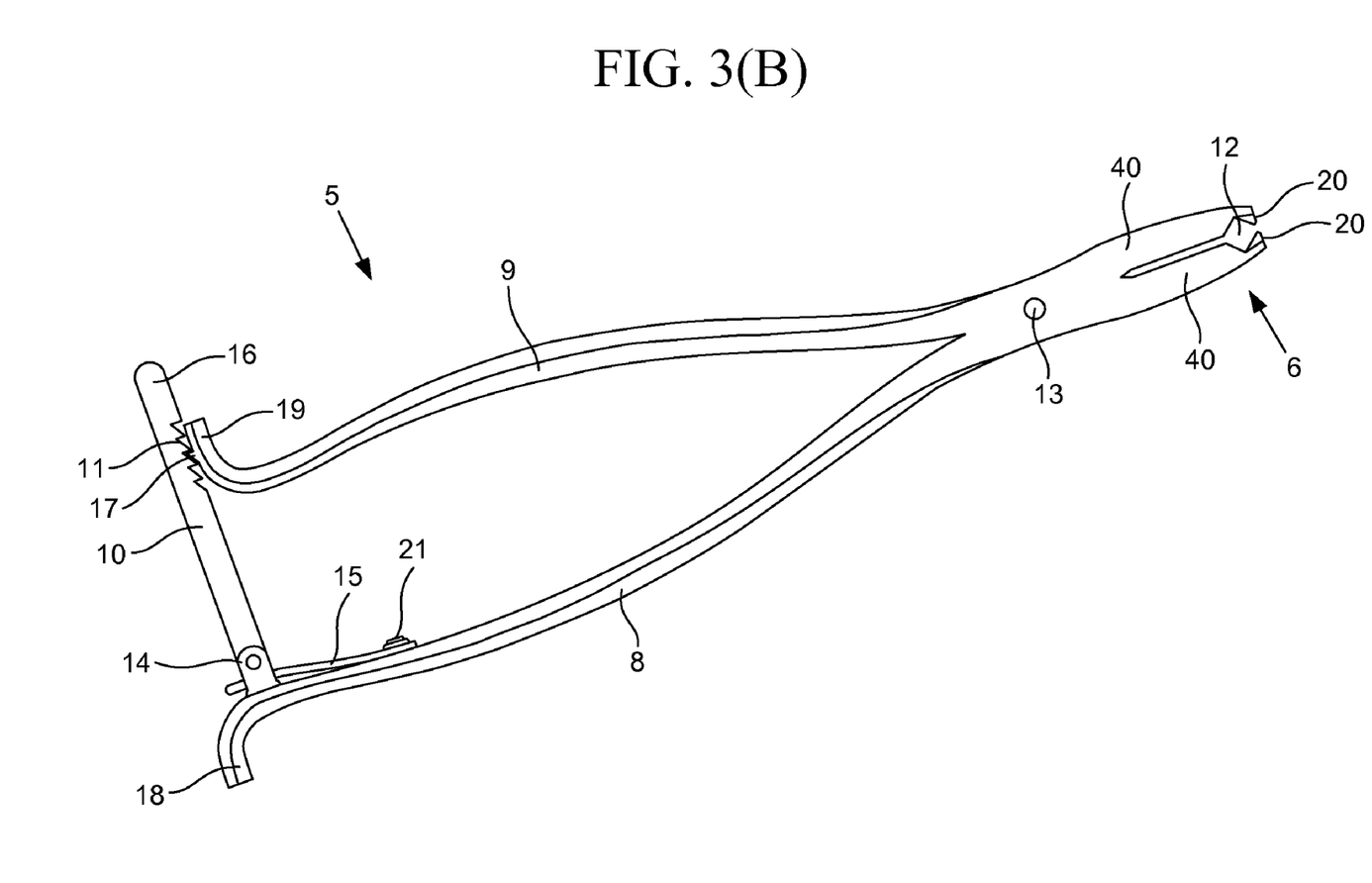

FIGS. 3(A) and 3(B) illustrate schematic diagrams of a rod holder 5 according to an embodiment of the invention. The rod holder 5 generally includes a tip end 6 and a handle end 7. The rod holder 5 further includes two gripping arms 8, 9 connected together by a pivot mechanism 13 such as a screw or pin to provide rotation means for the gripping arms 8, 9 to move in relation to one another. Furthermore, the handle end 7 of the rod holder 5 includes a locking mechanism 10 operatively connected to the gripping arms 8, 9. A first end 14 of the locking mechanism 10 operatively connects to a clip 15, which is connected to the gripping arm 8 via a retaining mechanism 21, such as a screw or pin. A second end 16 of the locking mechanism 10 comprises tooth-like features 11 defined thereon, which engage a corresponding tooth-like feature 17 configured on gripping arm 9. The rod holder 5 opens/closes in a scissor-like fashion, and generally has a square-shaped hole 12 in the area defined by the tip end 6 when the gripping arms 8, 9 are in the closed position. The gripping arms 8, 9 at the handle end 7 may be configured such that they terminate with a curved end 18, 19, which allows ease of manipulation by a user. Furthermore, the gripping arms 8, 9 at the tip end 6 each include a tip holder 40 having a prong tip 20.

Figures 4A, 4B, 4C:
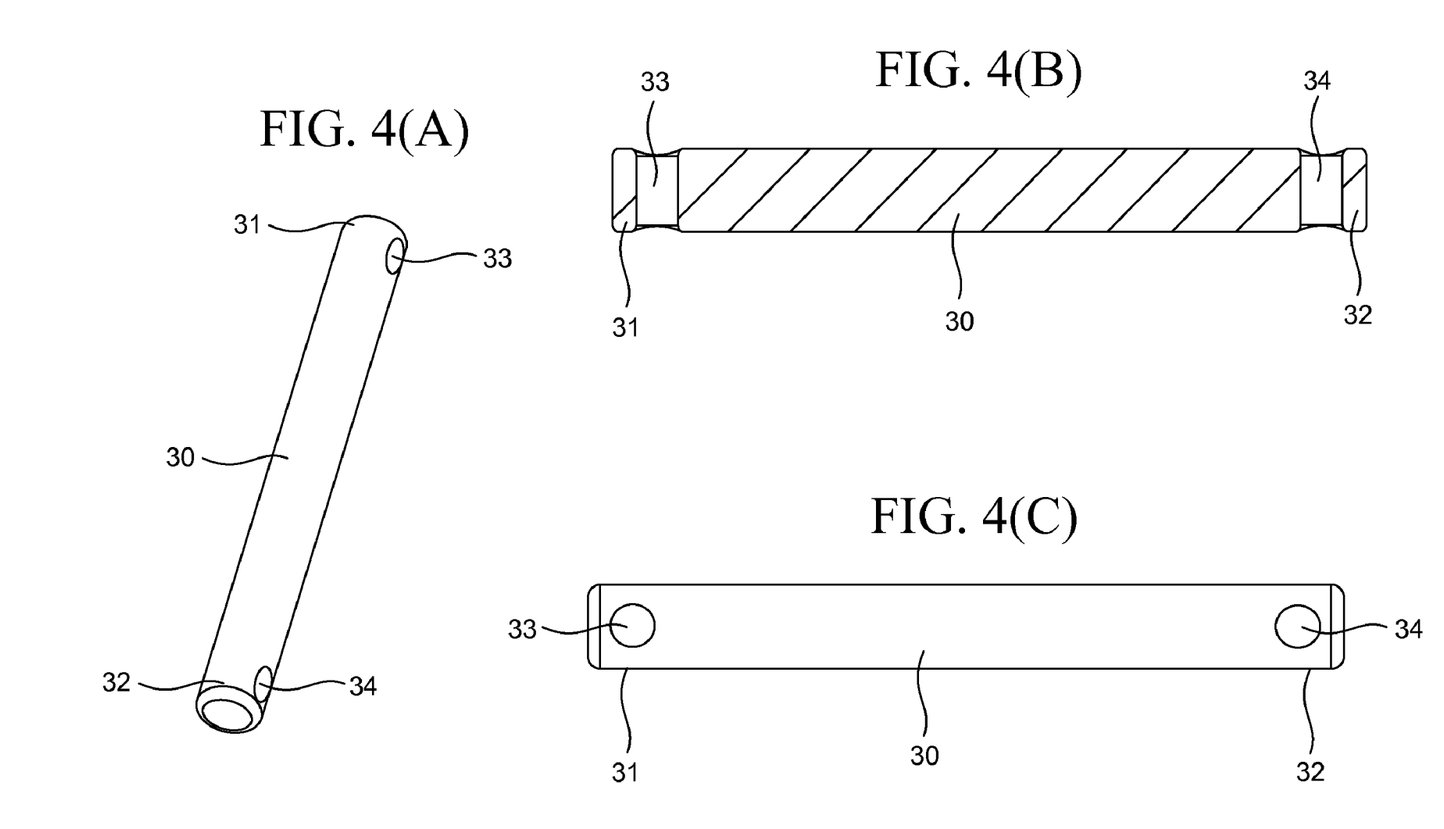
FIGS. 4(A) through 4(D) illustrate schematic diagrams of a rod according to an embodiment of the invention.
Figures 4D, 5A:
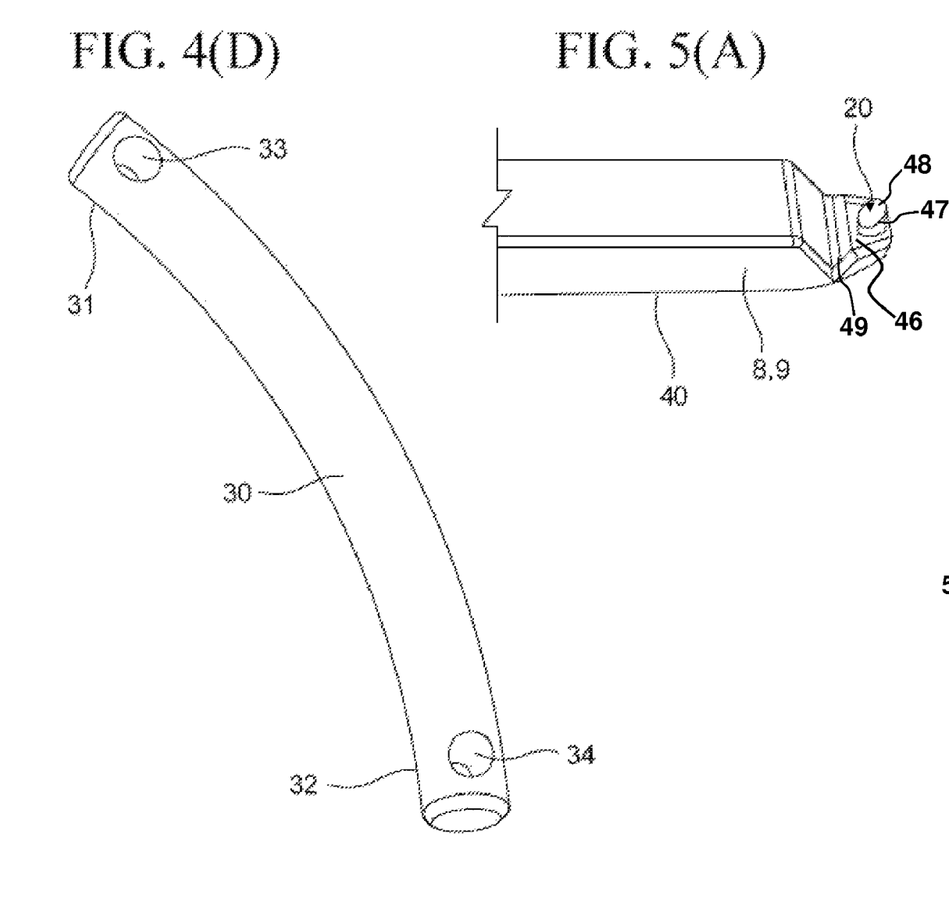
FIGS. 5(A) and 5(B) illustrate schematic diagrams of the tip end of the rod holder of FIGS. 3(A) and 3(B) according to an embodiment of the invention.

FIGS. 4(A) through 4(D) illustrate schematic diagrams of a longitudinal member 30 such as a rod according to an embodiment of the invention. FIG. 4(B) illustrates a cross-sectional view of the longitudinal member 30. FIGS. 4(A) through 4(C) illustrate the longitudinal member 30 in a straight configuration and FIG. 4(D) illustrates the longitudinal member 30 in a bent configuration. The rod 30 includes two distal ends 31, 32 each having a hole 33, 34 defined therein. The rod 30 is preferably rod-shaped (i.e., cylindrical). However, the rod 30 may assume other non-cylindrical shapes and could include bars or other types of longitudinal members.

Figure 5B:
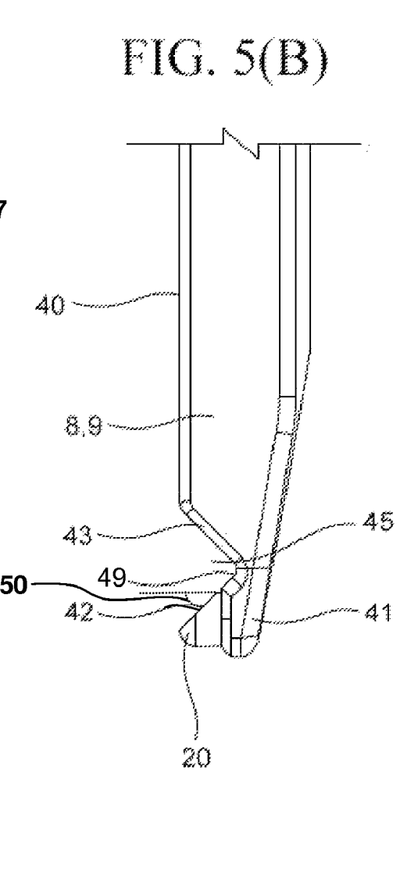

FIGS. 5(A) and 5(B) illustrate schematic diagrams of the tip holder 40 of the tip end 6 of the rod holder 5 of FIGS. 3(A) and 3(B) according to an embodiment of the invention. Each tip holder 40 includes a prong tip 20 positioned at the end of the tip holder 40 to allow for gripping of the rod 30 (of FIGS. 4(A) through 4(D)), whereby the gripping prong tip 20 is dimensioned and configured to engage the holes 33, 34 of the rod 30. The prong tip 20 is positioned on a base 41, which forms an end of each of the gripping arms 8, 9. The prong tip 20 is dimensioned and configured to have a sloping wall 42, which generally aligns with a sloping surface of the base 41. A corresponding sloping wall 43 of each of the gripping arms 8, 9 forms a notch 45 in each gripping arm (8 or 9) such that when both gripping arms 8, 9 are in the closed position, the notch 45 from each gripping arm (8 or 9) form a square-shaped hole 12 as indicated in FIGS. 3(A) and 3(B). In the embodiment shown in FIG. 5(A), prong tip 20 is situated on a planar base surface 46 and includes a wedge 47 that includes a prong tip sloping wall 48 that is angle 50 (e.g., 45 degrees) from planar base surface 46. In addition, planar base surface 46 is at an oblique angle to sloping wall 49. In the embodiment shown in FIGS. 5(A) and 5(B), notch 45 is formed by a 90 degree angle between sloping wall 43 and the combination of sloping wall 49 and prong tip sloping wall 48.

Figure 6:
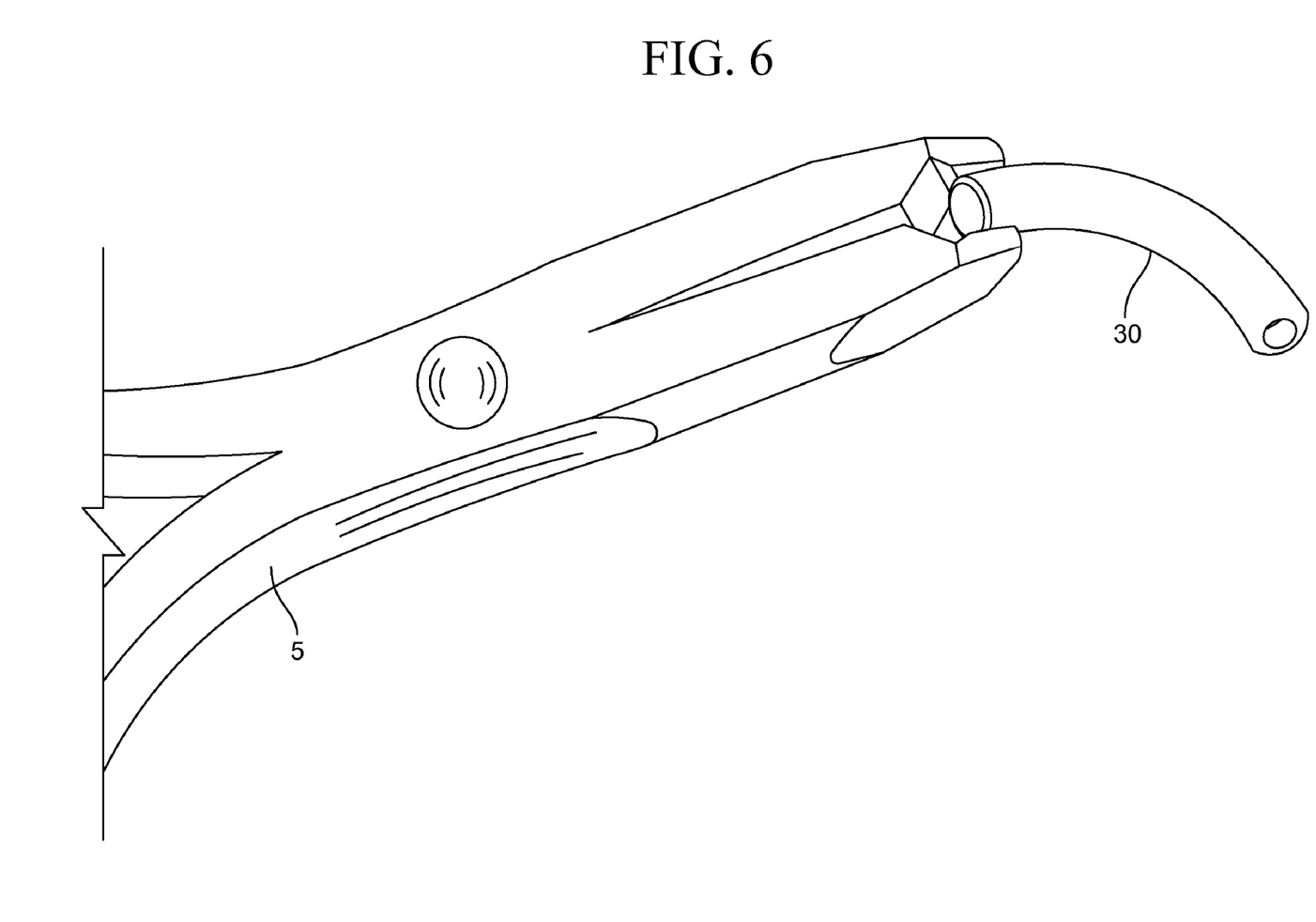
FIGS. 6 through 8 illustrate schematic diagrams of a rod holder manipulating a rod according to an embodiment of the invention.
Figure 7:
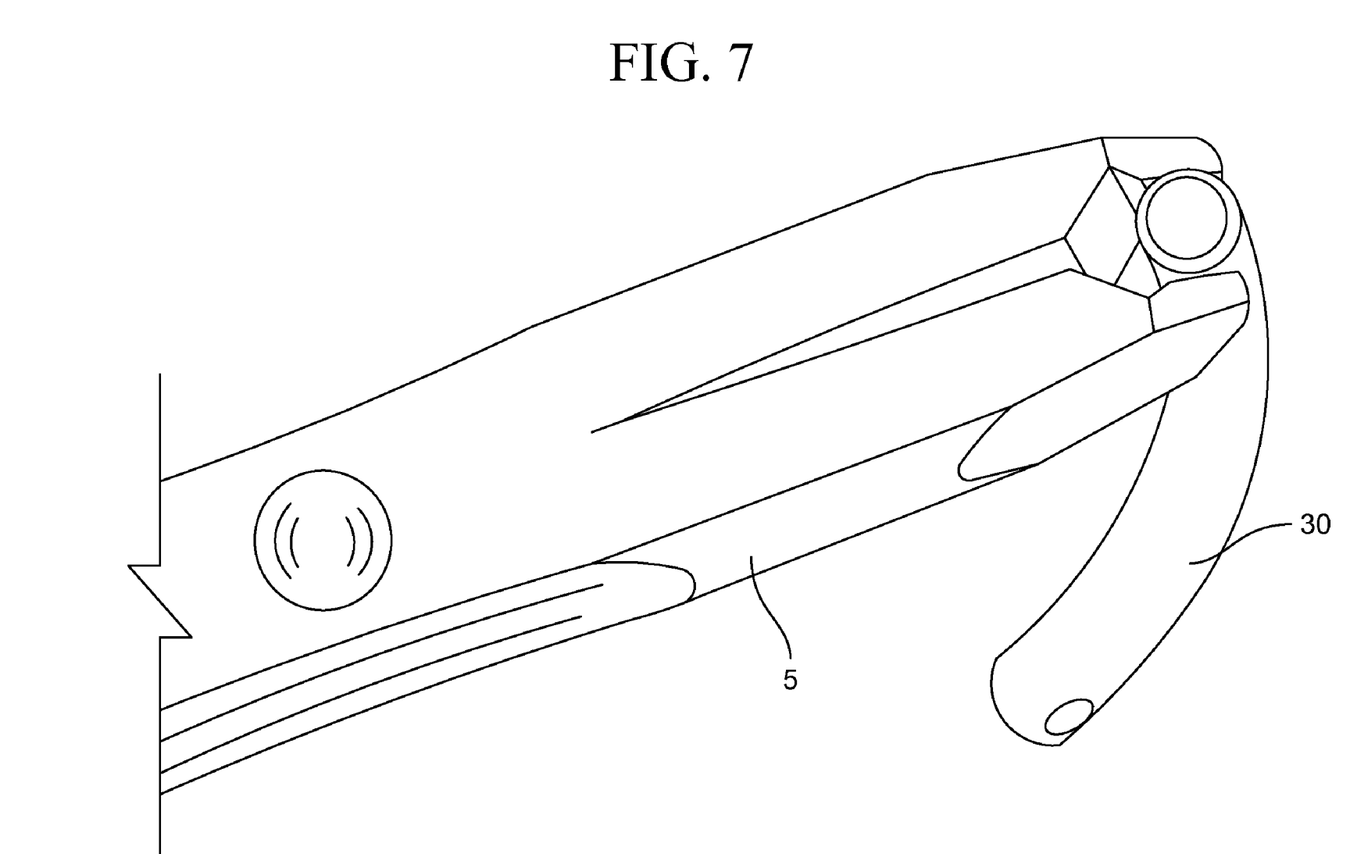
Figure 8:
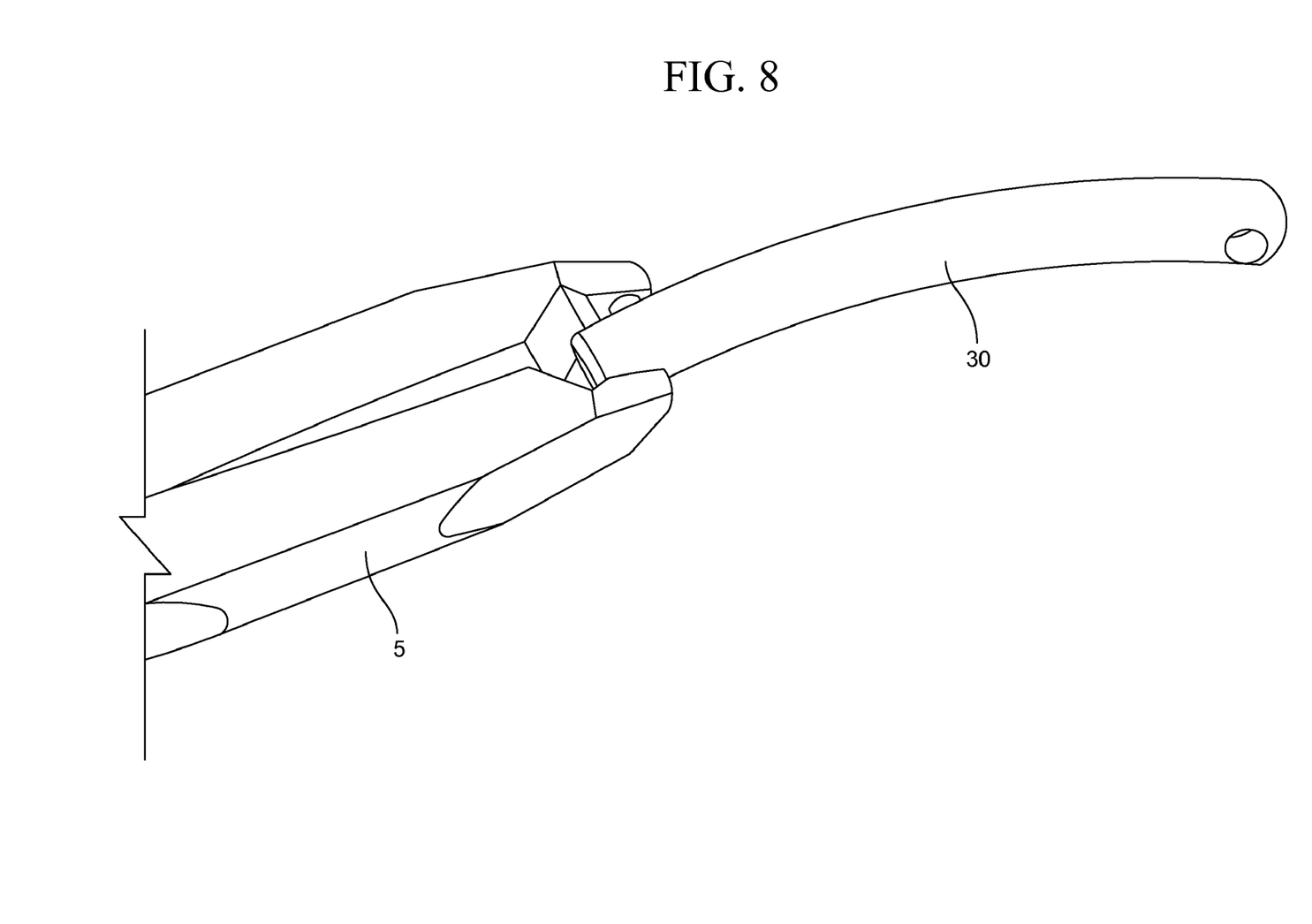

FIGS. 6 through 8 illustrate schematic diagrams of the rod holder 5 (of FIGS. 3(A) and 3(B)) manipulating a rod 30 (of FIGS. 4(A) through 4(D)) according to an embodiment of the invention. For example, FIG. 6 illustrates the rod 30 in a "midway" position in the rod holder 5. FIG. 7 illustrates the rod 30 in a "final" position in the rod holder 5. In this context, there is no difference between the "midway" position and the "final" position. FIG. 8 illustrates the rod 30 being articulated (approximately a 70-80° rotation) by the rod holder 5 in such a manner as to be inserted into the area of the spine (not shown) where it is to be located.

Figure 9:
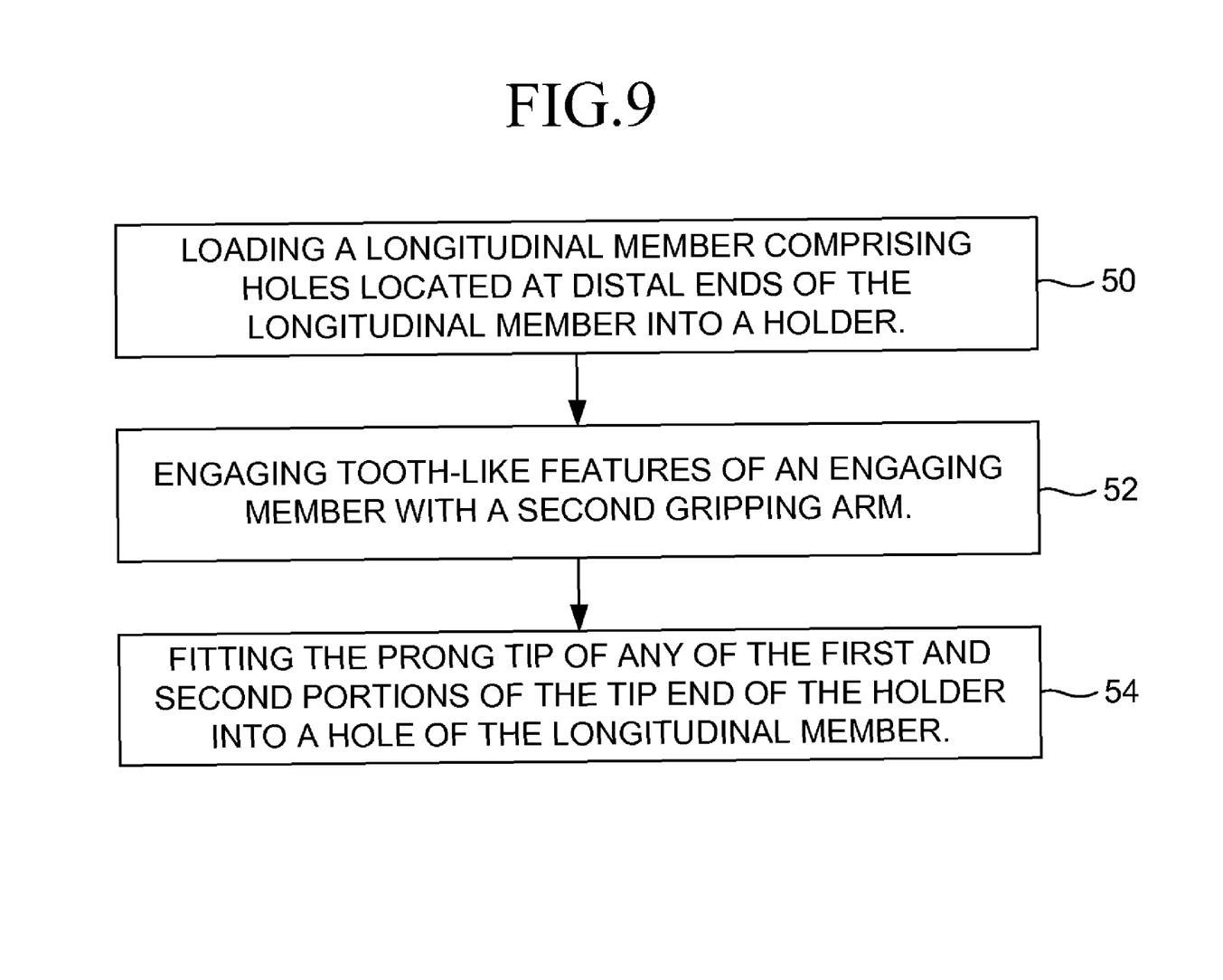
FIG. 9 is a flow diagram illustrating a preferred method according to an embodiment of the invention.

FIG. 9 (with reference to FIGS. 3(A) through 8) illustrate a method of inserting a longitudinal member 30 in a bone anchor (not shown) in a vertebral body (not shown), wherein the method comprises loading (50) a longitudinal member 30 comprising holes 33, 34 located at distal ends 31, 32 of the longitudinal member 30 into a holder 5, wherein the holder 5 comprises a tip end 6 comprising a first portion 8 and a second portion 9, wherein any of the first portion 8 and the second portion 9 comprise a prong tip 20; a handle end 7 located distally away from the tip end 6, wherein the handle end 7 comprises a first gripping arm 8, 18 and a second gripping arm 9, 19; and an engaging member 10 operatively connecting the first gripping arm 8, 18 to the second gripping arm 9, 19, wherein the engaging member 10 comprises tooth-like features 11, and wherein the method further comprises engaging (52) the tooth-like features 11 of the engaging member 10 with the second gripping arm 9, 19; and fitting (54) the prong tip 20 of any of the first and second portions 8, 9 of the tip end 6 of the holder 5 into a hole 33, 34 of the longitudinal member 30.

The method may further comprise positioning the longitudinal member 30 to be parallel to the holder 5; and inserting the longitudinal member 30 vertically into a desired location in the vertebral body (not shown) or a tissue retractor tube (not shown). Preferably, the second gripping arm 9, 19 comprises a protruding member 17, and wherein the method further comprises engaging the protruding member 17 of the second gripping arm 9, 19 with the tooth-like features 11 of the engaging member 10. Preferably, each of the first portion and the second portion 8, 9 of the tip end 6 comprises a notch 45 dimensioned and configured to form a generally square hole 12 when the first portion 8 and the second portion 9 are in a closed position. The method may further comprise pivoting the first gripping arm 8, 18 relative to the second gripping arm 9, 19. Furthermore, the method may further comprise pivoting the first portion 8 relative to the second portion 9. Additionally, the method may further comprise rotating the longitudinal member 30 when the longitudinal member 30 is engaged by the prong tip 20.

Generally, the embodiments of the invention provide a rod holder/inserter and method of holding/inserting a rod into a vertebral body, wherein the rod inserter holds a rod in a vertical or semi-vertical position from one end and allows the rod to be inserted and then rotated into its final horizontal position inside a wound. The embodiments of the invention can be used in spinal surgeries, where top or side loading bone anchors (not shown) are implanted or inserted in vertebral bodies (not shown). A rod holder 5 is used to insert the rod 30 through two or more of the bone anchors (not shown). For the rod holder 5 to function in the non-traditional sense, the rod 30 includes a hole 33, 34 through one or both ends 31, 32 of the rod 30.

During a traditional open procedure, the rod holder 5 functions as does a standard off-the-shelf holder. However, in a "MIS" (minimally invasive surgery) procedure, the incision is much smaller, or through a tube that functions as a tissue retractor. These tubes are typically between 18 to 15 mm in diameter. The rod 30 is then loaded onto the rod holder 5 by locating the hole (either 31 or 32) at one end of the rod 30. Once the rod 30 is loaded parallel with the rod holder 5, it can be inserted vertically into the wound or tube (not shown), then by releasing the pressure the rod holder 5 applies to the rod 30, the rod 30 can be rotated, manipulated, and inserted into the bone anchors (not shown). Accordingly, the embodiments of the invention provide a modification of a widely available instrument to function in both the traditional sense as well as a novel means to insert a long spinal rod 30 through a small opening by gripping it securely, yet allowing the rod 30 to rotate into the horizontal position for MIS procedures.

The foregoing description of the specific embodiments will so fully reveal the general nature of the invention that others can, by applying current knowledge, readily modify and/or adapt for various applications such specific embodiments without departing from the generic concept, and, therefore, such adaptations and modifications should and are intended to be comprehended within the meaning and range of equivalents of the disclosed embodiments. It is to be understood that the phraseology or terminology employed herein is for the purpose of description and not of limitation. Therefore, while the embodiments of the invention have been described in terms of preferred embodiments, those skilled in the art will recognize that the embodiments of the invention can be practiced with modification within the spirit and scope of the appended claims.

What is claimed is:

1. A method of using a medical device in a surgical procedure, said method comprising:
providing a longitudinal member comprising a single, generally cylindrical and uniformly constructed rod, with a single first hole bored through a first end of said rod and a single second hole bored through a second end of said rod, wherein said rod is positioned along a longitudinal axis of said longitudinal member, and said hole is positioned transverse to said longitudinal axis of said longitudinal member;
providing a holder comprising:
a first tip end comprising a first portion comprising a first portion sloping wall and a first base continuously coupled to said first portion and stacked atop said first portion, said first base comprising a single outwardly projecting unslotted first prong tip continuously coupled said first base and stacked atop said first base and configured to engage said first hole of said longitudinal member, said first prong comprising a first prong sloping wall comprising a first planer surface at an oblique angle from said first base;
a second tip end comprising a second portion comprising second portion sloping wall and a second base continuously coupled to said second portion and stacked atop said second portion, said second base comprising a single outwardly projecting unslotted second prong tip continuously coupled said second base and stacked atop said second base and configured to engage said second hole of said longitudinal member, said second prong comprising a second sloping wall comprising a planer surface at an oblique angle from said second portion;

a handle end located distally away from said first tip end and said second tip end, wherein said handle end comprises a first gripping arm and a second gripping arm, wherein said first gripping arm comprises a first curved end forming a 90 degree curve pointing in a direction parallel to and away from said first prong tip and said second gripping arm comprises a second curved end forming a 90 degree curve pointing in a direction parallel to and away from said second prong tip; and an engaging member operatively connecting said first gripping arm to said second gripping arm, wherein said engaging member comprises tooth-like features positioned facing said tip end, wherein said first portion sloping wall and said first prong sloping wall form a first-wedge comprising 45 degree angle, and wherein said second portion sloping wall and said second prong sloping wall form a second wedge comprising a 45 degree angle; and engaging said tooth-like features of said engaging member to said curved end of said second gripping arm.

2. The method of claim 1, wherein said second gripping arm comprises a protruding member dimensioned and configured to engage that engages said tooth-like features of said engaging member.

3. The method of claim 1, said first wedge and said second wedge comprise a notch that forms a generally diamond-shaped hole when said first portion and said second portion are in said closed position.

4. The method of claim 1, wherein said first portion and said second portion rotate about a fixed axis with respect to one another.

5. The method of claim 1, further comprising operatively connecting said first portion to said second portion.

6. The method of claim 1, wherein said first prong tip and second prong tip each are cylindrically-shaped.

7. The method of claim 1, wherein said longitudinal member is rotatable when engaged by said first prong tip and said second prong tip.

8. A method comprising:

providing a medical device comprising a pair of arms comprising a first arm and a second arm, wherein each arm comprises:

a tip end comprising a tip end sloping wall, said tip end sloping wall comprises a first 45 degree sloping surface, and a tip holder coupled to said tip end and stacked atop said tip end, said tip holder comprising a base coupled to said tip holder and stacked atop said tip holder, said base comprising an outwardly projecting unslotted prong tip stacked atop said base, wherein said prong tip comprises a prong tip sloping wall, said prong tip sloping wall comprises a second 45 degree sloping surface, and said tip end sloping wall and said prong tip sloping wall form a 90 degree wedge therebetween;

a handle end located distally away from each said tip end, wherein each said handle end comprises a gripping arm, wherein each gripping arm comprises a curved end forming a 90 degree curve pointing in a direction parallel to and away from said prong tip of each said tip end corresponding to each said handle end, and wherein said handle end terminates where said curved end is in a direction parallel to and away from said prong tip of each said tip end corresponding to each said handle end; and operatively connecting said pair of arms together using an engaging member comprising tooth-like features positioned facing said tip end.

9. The method of claim 8, wherein said gripping arm comprises a protruding member that engages said tooth-like features of said engaging member.

10. The method of claim 8, wherein said tip end of each arm further comprises a notch and said notch of said tip end forms a square hole when said pair of arms are in a closed position.

11. The method of claim 8, further comprising operatively connecting said pair of arms together.

12. The method of claim 8, further comprising providing only one pivoting connection between said tip ends.

13. The method of claim 8, wherein said tooth-like features of said engaging member are dimensioned and configured to engage said curved end of one said gripping arm.

* * * * *